(12) United States Patent
Ruppert

(10) Patent No.: US 6,250,134 B1
(45) Date of Patent: Jun. 26, 2001

(54) APPARATUS FOR DETERMINING THE DEW-POINT AND/OR THE CONTENT OF VAPOR IN THE AIR

(75) Inventor: Paul Ruppert, Wetzikon (CH)

(73) Assignee: Meteolabor AG, Wetzikon (CH)

( * ) Notice: Subject to any disclaimer, the term of this patent is extended or adjusted under 35 U.S.C. 154(b) by 0 days.

(21) Appl. No.: 09/250,048

(22) Filed: Feb. 12, 1999

(30) Foreign Application Priority Data

Mar. 16, 1998 (CH) .................................................. 0620/98

(51) Int. Cl.[7] .................................................. G01N 25/66
(52) U.S. Cl. ..................... 73/29.01; 73/29.02; 73/29.05; 73/335.01; 374/16; 374/17; 374/18; 374/19; 374/20; 374/28
(58) Field of Search ............................... 73/29.01, 29.02, 73/29.05, 335.01, 73; 374/16, 17, 18, 19, 20, 28

(56) References Cited

U.S. PATENT DOCUMENTS

| 2,624,195 | * | 1/1953 | Van Alen ................................ 374/20 |
| 3,037,387 | * | 6/1962 | Friedman et al. ....................... 374/20 |
| 4,035,644 | * | 7/1977 | Ciemochowski ........................ 374/20 |
| 5,615,954 | * | 4/1997 | Nishizawa et al. ..................... 374/17 |

FOREIGN PATENT DOCUMENTS

| 1561114 | * | 2/1980 | (GB) .................................... 374/208 |
| 1927 | * | 2/1992 | (WO) .................................... 374/16 |

* cited by examiner

Primary Examiner—Daniel S. Larkin
(74) Attorney, Agent, or Firm—Tarolli, Sundheim, Covell, Tummino & Szabo L.L.P.

(57) ABSTRACT

The apparatus for determining the dew-point and/or the content of vapor in the air, particularly for the use in radio sondes, comprises a dew-point mirror assembly, including a source of light, a reflector, a cooling element thermally coupled to the reflector, a temperature sensor for measuring the temperature of the reflector, and a detecting sensor for receiving the light emitted by the light source and reflected by the reflector. The detecting sensor is located in a temperature stabilized region of the apparatus and optically coupled to the reflector by means of a light wave conductor. The light source is an incandescent lamp. A sensor head is provided that receives the reflector, the cooling element, the light source, and the input end of the light wave conductor. The sensor head is heated by means of an active heating element. For exactly determining the temperature of the reflector, a combination thermo element/reflector is proposed, whereby the thermo element is constituted by two sheet metal plate members soldered to each other face to face. The surface of one of the sheet metal plate members is highly reflective and constitutes the reflector. With the help of such an apparatus, the dew-point and/or the content of vapor in the air can be determined very accurately.

17 Claims, 3 Drawing Sheets

APPARATUS FOR DETERMINING THE DEW-POINT AND/OR THE CONTENT OF VAPOR IN THE AIR

BACKGROUND OF THE INVENTION

The present invention refers to an apparatus for determining the dew-point and/or the content of vapor in the air, particularly for the use in radio sondes. The apparatus comprises a dew-point mirror assembly, including a source of light, a reflector, a cooling element thermally coupled to the reflector, a temperature sensor for measuring the temperature of the reflector and a detecting sensor that receives the light emitted by the light source and reflected by the reflector. Included in the apparatus is a space or region that receives temperature sensitive components of the dew-point mirror assembly, whereby means are provided for stabilizing the temperature in this space or region.

In order to determine the content of vapor in the free atmosphere, radio sondes carried by a balloon are used as a matter of routine nowadays. Thereby, frequently the so-called adsorption moisture sensors are used that operate with the help of a hygroscopic plastic film. Reasonable results can be obtained with the aid of those sensors in a temperature range of between +50° C. and −35° C. Below a temperature of −35° C., i.e. above approximately 7000 m height, depending on the weather and the latitude, the measurements are uncertain or not usable anymore because those sensors stop operating. The reason for that limit of possible measurements can be found in the physics of the adsorption measurement method.

For this reason, dew-point mirror assemblies are used more and more nowadays. The measuring method using those dew-point mirror assemblies is simple and well defined. A mirror is subjected to the air to be analyzed and cooled by means of a cooling element until it is misted up, i.e. until a condensate of water or, at lower temperatures, of ice is formed on its surface. Now, the temperature of the mirror is controlled in such a way that the condensate layer remains stable, i.e. the condensate layer does not evaporate and no new condensate is created. In this stable condition, the surface of the mirror has a temperature that corresponds to the vapor saturation temperature. The temperature of the surface of the mirror is measured by means of a thermometer integrated into the surface of the mirror. Based on the dew-point temperature and the simultaneously measured air temperature, the relative humidity of the air can be calculated.

PRIOR ART

In the dew-point mirror assemblies known in the prior art, the reflection characteristics of the mirror is checked by means of an opto-electronic circuitry. For this purpose, the surface of the mirror is illuminated by means of a light source radiating under an angle of 45° towards the mirror. In the known apparatuses, a semiconductor light source in the form of a light emitting diode (LED) is used as the light source. Opposite to the LED, there is provided a photo transistor, mounted under an angle of 45° as well, to measure the light reflected by the mirror. If the surface of the mirror is covered with condensate, a portion of the light is diffused by the water drops or ice crystals in all directions. Thus, less light is reflected to the photo transistor. The electric signal delivered by the photo transistor serves as instantaneous value in a control system that controls the current in the cooling element of the mirror and thereby keeps the reflection characteristics of the mirror in a stable condition.

By means of such dew-point mirror measurement apparatuses, accurate results can be obtained usually in a temperature range of between +50° C. and −40° C. However, at temperatures below −40° C. and particularly at low air humidity, where there is a great difference between air temperature and dew-point temperature, a limit is reached with the dew-point mirror measurement apparatuses hitherto used in radio sondes at which the required measurement accuracy or the operation thereof is no longer ensured.

This can be explained by the fact that the detecting sensor as well as most of the other electronic components are not specified to operate at temperatures below −40° C. In order to fix this problem, apparatuses are known in the art that are provided with a temperature stabilized region or space for receiving the temperature sensitive components. However, not all of the temperature sensitive components can be located in that temperature stabilized region because certain components, particularly the light source and the detecting sensor, are inevitably subjected or have to be inevitably subjected to the ambient air. Thus, the desired measurement accuracy cannot be ensured with these apparatuses as well.

Even if prototypes of dew-point mirror measurement apparatuses are known by means of which satisfying results can be obtained also at temperatures below −40° C., these apparatuses are not appropriate to be used in radio sondes since such dew-point mirror measurement apparatuses are very expensive, have a weight of up to several kilograms and require electrical power of 100 W and more. Due to the heavy weight and the enormous power consumption, they can be used on no account in radio sondes because the load carrying capacity of customary carrier balloons for radio sondes is limited.

OBJECTS OF THE INVENTION

Thus, it is an object of the invention to improve an apparatus for determining the dew-point and/or the content of vapor in the air of the kind referred to herein before in such a way that the apparatus supplies accurate measuring results also at very low temperatures while it is inexpensive, has a low weight and a low power consumption.

It is another object of the present invention to provide a method by means of which the presence of over-saturated air and/or air containing water drops or ice crystals can be recognized.

SUMMARY OF THE INVENTION

To meet these and other objects, the present invention provides, according to a first aspect, an apparatus for determining the dew-point and/or the content of vapor in the air, particularly for the use in radio sondes. The apparatus comprises a dew-point mirror assembly, including a source of light, a reflector, a cooling element thermally coupled to the reflector, a temperature sensor adapted to measure the temperature of the reflector and a detecting sensor that receives the light emitted by the light source and reflected by the reflector. Included in the apparatus is a space or region that receives temperature sensitive components of the dew-point mirror assembly, whereby means are provided for stabilizing the temperature in this space or region.

The detecting sensor is located in the temperature stabilized space or region, and the dew-point mirror assembly further comprises a light wave conductor. Thereby, the detecting sensor is optically coupled to the reflector by means of the light wave conductor.

In order to be in a position to determine the temperature of the mirror more accurately than up to now, the above mentioned temperature sensor can be designed as a thermo element. By the proposed design of the thermo element, parasitic heat flows caused by the temperature sensor can be avoided. Parasitic heat flows caused by the temperature sensor always arise if the mirror is very small and the temperature of the mirror is substantially lower than the ambient temperature. By means of the proposed reflector/thermo element combination, the above explained problems can be avoided to a very high degree and the temperature of the mirror can be determined more accurately.

According to a preferred embodiment, the apparatus comprises a sensor head containing the light source, the reflector, and the input end of the light wave conductor. Thereby, the apparatus is provided with a valve member for varying the flow cross section for the ambient air flowing through the sensor head. The valve member operates in dependence of the barometric pressure and the flow velocity of the ambient air flowing through the sensor head. By the provision of such a valve member, the apparatus can be constructively designed such that the heat transition between the housing of the sensor head and the ambient remains within certain limits, even if the barometric pressure and the flow velocity varies. Such a valve member provides great advantages if the apparatus is used in radio sondes, since a radio sondes passes a range of barometric pressure of between 1000 hPa and 5 hPa during its ascent to a height of 35 kilometers. Thereby, the heat dissipation of the heated sensor head should not be too high in low heights, and in great heights a sufficient heat dissipation from the warm side of the cooling element, located in the sensor head as well, should be ensured.

According to a second aspect, the invention provides a method for recognizing over-saturated air and/or air containing water drops or ice crystals. The method is performed with the aid of the apparatus as described in this invention and comprises the following steps:

The air in the interior of the sensor head is heated in order to evaporate water drops or ice crystals. Then, the temperature of the ambient air is measured and the dew-point temperature is determined. Thereafter, the temperature of the ambient air is subtracted from the dew-point temperature and the temperature difference is calculated. Finally, an over-saturation of the air or the presence of water in fluid or solid form in the air is recognized if the calculated temperature difference is positive. Moreover, the amount of fluid or solid water contained in a given air volume can be calculated on the basis of the calculated temperature difference.

Brief Description of the Drawings

In the following, an embodiment of the apparatus according to the invention will be further described, with reference to the accompanying drawings, in which.

Detailed Description of a Preferred Embodiment

Figure 1:
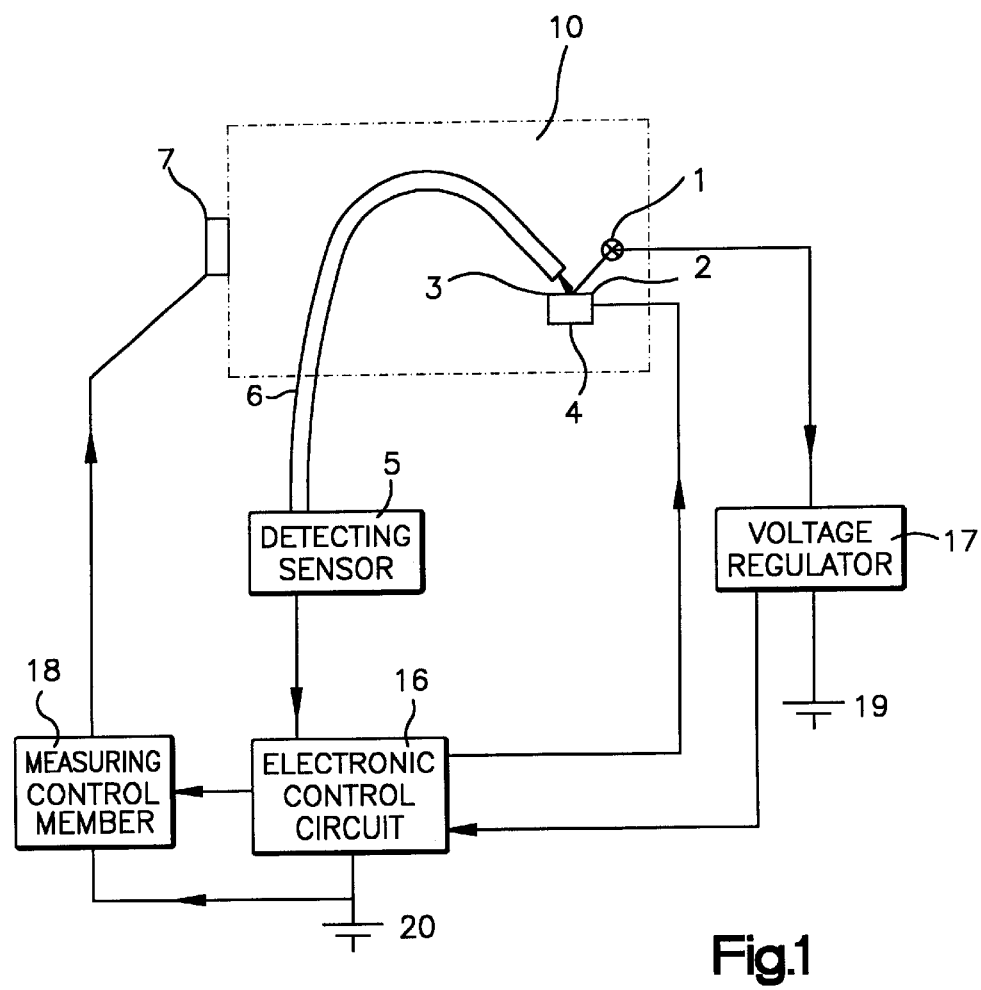
FIG. 1 shows a functional diagram of the apparatus.

In the following, the general layout and the mode of operation of the apparatus shall be further explained with the help of FIG. 1. The apparatus comprises a dew-point mirror assembly that essentially includes a light source 1, a reflector 2, a temperature sensor 3, a cooling element 4, a detecting sensor 5, and an electronic control circuit 16. The light source 1 is received, together with the reflector 2 and the temperature sensor 3, in a sensor head 10. Moreover, there is provided a light wave conductor 6 that is led into the sensor head 10 in order to optically couple the detecting sensor 5 with the reflector 2. In order to be in a position to heat the sensor head 10, there is provided a heating element 7. Furthermore, a voltage regulator 17 as well as a heating control member 18 are provided and located, together with the detecting sensor 5 and the electronic control circuit 16, in a region of the apparatus whose temperature is stabilized. That temperature stabilized region is constituted by a thermally insulated housing in which is received a heat reservoir, for example in the form of a bag filled with water. Finally, for supplying power to the apparatus, two batteries 19 and 20 are provided.

Since a person skilled in the art knows the mode of operation of a dew-point mirror and of a dew-point hygrometer, only the elements and their mode of operation will be explained in more detail that are relevant in connection with the present invention. It should be noted that the second temperature sensor required for determining the relative humidity of the air is not illustrated.

As a light source 1, an incandescent lamp is provided that illuminates the reflector under an angle of 45°. The light reflected by the reflector 2 is received by the light wave conductor 6, positioned under an angle of 45° as well, and led to the detecting sensor 5. The temperature of the reflector 2 is measured by means of a thermo element 3. The cooling element 4 is designed as a Peltier element. The afore mentioned electronic control circuit 16 is used for controlling the temperature of the Peltier element 4 and, thereby, of the reflector 2. Finally, the sensor head 10 also contains the heating element 7 in the form of a transistor. Thereby, the housing of the sensor head 10 can be heated, if required. The transistor 7 is driven by a heating control member 18 that activates the transistor 7 in dependence of the cooling power of the cooling element 4. If the cooling power drops towards zero, the dew-point temperature approximates the air temperature. Thus, at positive temperatures, the danger exists that water deposits on the surface of the sensor head 10, with the result that the dew-point mirror is no longer operative.

Consequently, the heating element 7 of the sensor head 10 is activated as soon as the difference between the dew-point temperature and the air temperature falls short of a predetermined value. In this way, a moistening of the sensor head 10 can be reliably avoided.

However, heating the sensor head 10 offers additional possibilities because thereby, for example, the presence of clouds can be detected:

If a temperature is measured on the surface of the reflector 2 that is higher than the air temperature, this means that water or ice crystals are present in the air and, consequently, that the radio sondes traverses a cloud. The explanation therefore is based on the fact that the air in the heated sensor head 10 is heated and that its absolute moisture content rises due to the rise in the temperature, provided that water drops or ice crystals are present in the air and have been evaporated. In this case, the measured dew-point temperature is higher than the air temperature. Based on that difference between dew-point temperature and air temperature, moreover, a quantitative statement is possible as far as the water content of the air is concerned. By providing a heating element 7 in the sensor head 10, clouds can be recognized and their water content in fluid or solid form can be determined for the first time.

Figure 2:
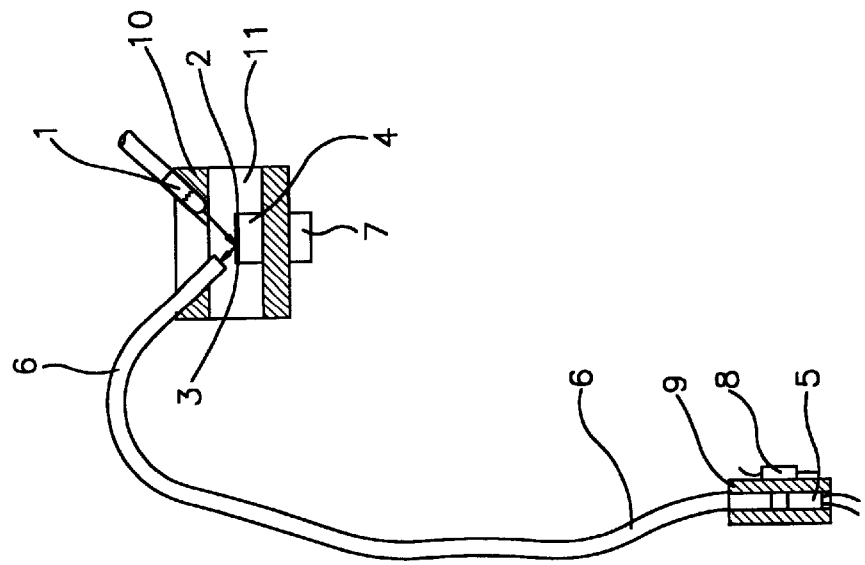
FIG. 2 shows a schematic view of a dew-point mirror assembly.

FIG. 2 shows a schematic view of the dew-point mirror assembly. In this illustration, it can be seen that the Peltier element 4, together with the thermo element 3 and the reflector 2, are located in a flow channel 11 of the sensor head 10. As far as the thermo element 3 is concerned, it is constituted by two sheet metal plate members consisting of copper and constantan, respectively, that are soldered to each other in such a way that at least a portion of their facing surfaces touch each other. The sheet metal plate member made of constantan is gold-plated on its exposed surface to constitute the reflector 2, while the sheet metal plate member made of copper is glued onto the cold surface of the Peltier element 4. The design of the thermo element will be explained herein after with reference to FIG. 4 in more detail. The incandescent lamp 1 as well as the input end of the light wave conductor 6 is received in the wall of the sensor head 10. The transistor 7 operating as a heating element is located at the lower side of the sensor head 10.

The other end, i.e. the output end of the light wave conductor 6 is received in a housing 9. In the same housing 9, the detecting sensor 5 is located whereby, in the present example, a photo transistor 5 is used as a detecting sensor. For compensating the temperature in the case of temperature fluctuations, a thermistor 8 is provided.

The use of an incandescent lamp 1 as the light source offers the advantage that its emission characteristics do not change upon fluctuations of the ambient temperature, strictly in contrary to the behavior of semiconductor light sources.

Figure 3:
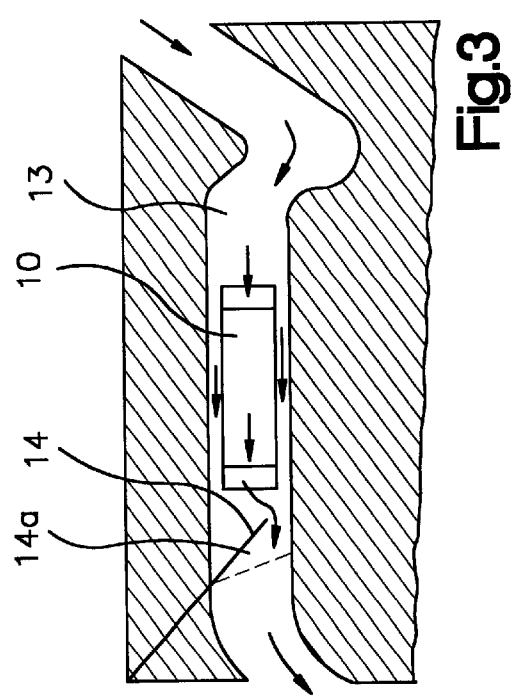
FIG. 3 shows a cross sectional view of a schematically illustrated sensor head.

FIG. 3 shows a cross sectional view of a schematically illustrated portion of an air channel 13 of the apparatus in which the sensor head 10 is located. As seen in the direction of the flow of the air, a valve plate member 14 is mounted behind the sensor head 10 that is resiliently biased. The valve plate member 14 moves under the influence of the air flow in such a way that the flow cross section of the air channel 13 is less at a high barometric pressure, i.e. in modest heights, than at a low barometric pressure, i.e. in great heights. Since the climb rate of a radio sondes is relatively constant during its ascent, with the result that the flow velocity of the air through the air channel 13 is steady, the deflection of the valve plate member 14 is influenced essentially only by the barometric pressure. In FIG. 3, the dashed line 14a indicates the deflection of the valve plate member at high barometric pressure.

Figure 4:
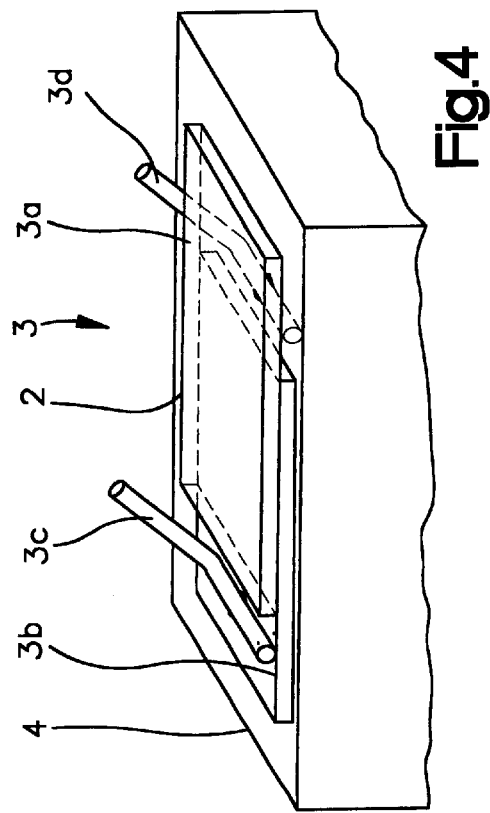
FIG. 4 shows a detailed view of a reflector thermo element.

FIG. 4 shows a detailed view of the thermo element 3 that is simultaneously designed as a reflector. As it has been explained herein above, the thermo element comprises two sheet metal plate members 3a, 3b whose facing surfaces are soldered together. The lower sheet metal plate member 3b is made of copper and the upper sheet metal plate member 3a is made of constantan. The two sheet metal plate members 3a, 3b only partially overlap, whereby the overlapping portions are soldered to each other. A connecting wire 3c, consisting of copper, is welded to the free, not overlapping portion of the lower sheet metal plate member 3b made of copper, while a connecting wire 3d, consisting of constantan, is welded to the free, not overlapping portion of the upper sheet metal plate member 3a made of constantan. The thermo voltage is created within the thermo element at the soldered portion of the two sheet metal plate members 3a, 3b. The free surface of the sheet metal plate member 3a made of constantan is gold-plated to thereby constitute the reflector, while the sheet metal plate member 3b made of copper is glued to the cold surface of the Peltier element 4. In practice, the size of the two sheet metal plate members 3a, 3b is in the region of a few millimeters only.

Such a construction results in nearly ideal thermodynamic characteristics for the measurement of the temperature, since parasitic heat flows, getting into the mirror, i.e. the reflector, particularly through the connecting wires, can be eliminated to a very high degree and do not have any influence on the accuracy of the measurement of the temperature in the present embodiment.

Figure 5:
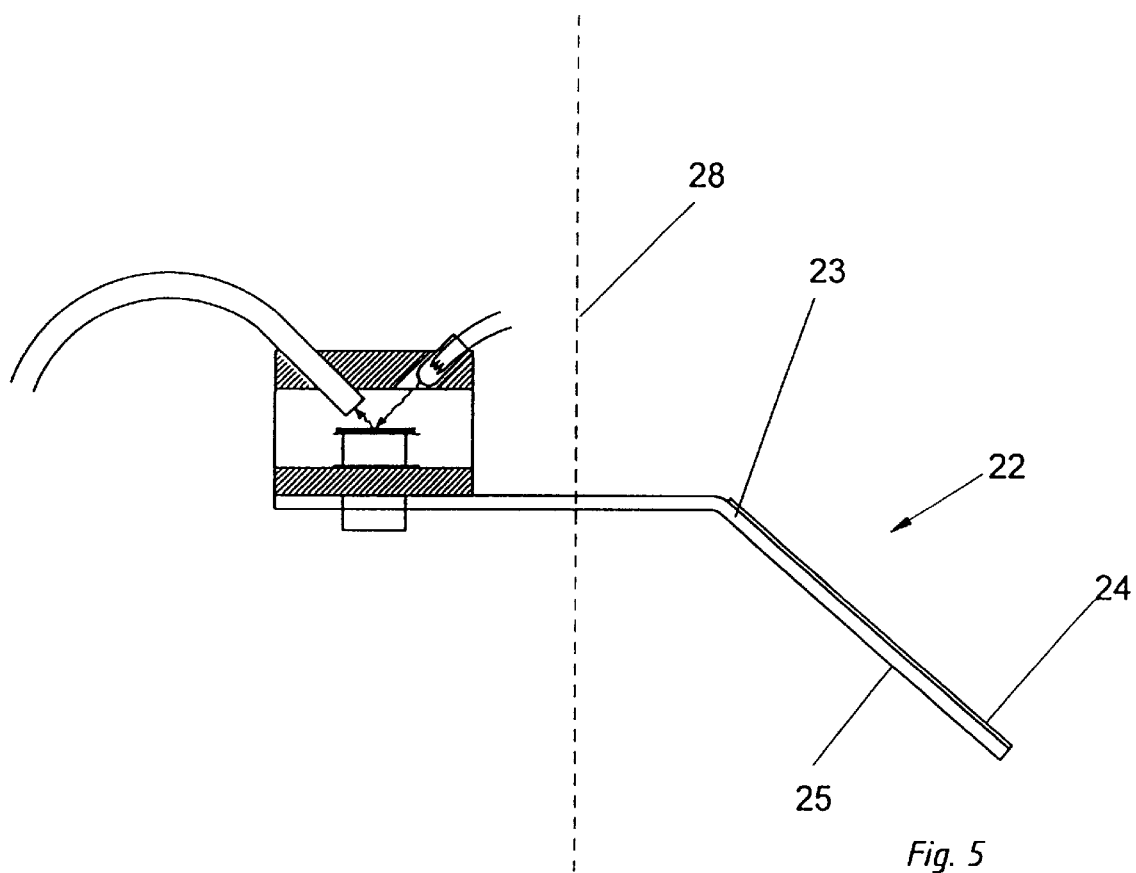
FIG. 5 shows a schematic lateral view of an infrared radiator.
Figure 5A:
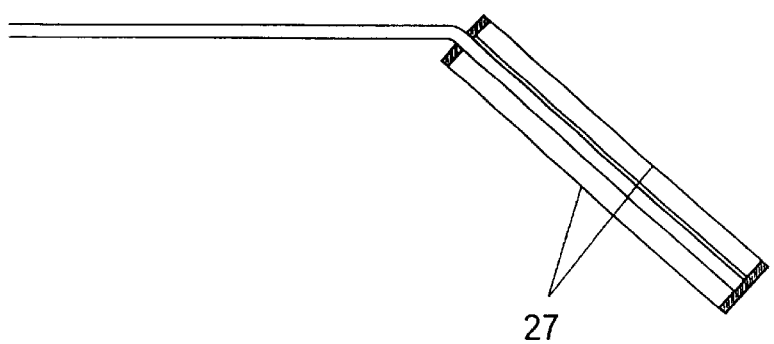
FIG. 5a shows a partial lateral view of an alternative embodiment of the infrared radiator.

Since the maximally achievable temperature depression of the dew-point mirror is reduced in great heights due to the temperature dependent characteristics of the cooling element 4 and due to the worse heat dissipation of the warm surface of the cooling element 4, a low relative air humidity cannot be measured and cannot be measured with the required accuracy, respectively, from a certain height on upwards. But as a matter of fact, just in the stratosphere, the relative air humidity is small. This problem can be solved, at least during the night, by means of an infrared radiator 22, as illustrated in FIGS. 5 and 5a.

The infrared radiator 22 comprises an angled sheet metal plate member 23 that is provided with a black painted upper surface 24 and a polished lower surface 25. The sheet metal plate member 23 is thermally connected to the warm surface of the cooling element 4. The infrared radiator 22 laterally projects out of the housing of the radio sondes, whereby the wall of the sensor head 10 is schematically indicated by the dashed line 28 in FIG. 5. In order to reduce the influence of convection on the infrared radiator 22, the upper surface 24 and the lower surface 25 of the infrared radiator 22 can be thermally insulated by an infrared permeable plastic foil 27, as shown in FIG. 5a.

By providing an infrared radiator 22 of the design as explained herein before, it is no longer necessary that the heath from the warm side of the cooling element is passed to the ambient air only by convection, since the infrared radiator 22 radiates energy with a great wavelength from its upper surface 24 to the space. It is understood that the upper surface 24 of the infrared radiator 22 is that surface that faces the space and that the lower surface 25 of the infrared radiator 22 is that surface that faces the earth. In order to swivel the infrared radiator 22 between a rest position and an operating position, for example a (not shown) hinge could be provided. Thus, during daytime, the infrared radiator 22 is preferably swiveled into its rest position in which it is located in the interior of the radio sondes, while it is swiveled into its operating position outside the housing of the radio sondes during the night.

To sum up, it can be recorded that the accuracy of the measurement is substantially increased by locating the detecting sensor 5 in a temperature stabilized region of the apparatus and by providing a light wave conductor extending between the reflector 2 and the detecting sensor 5, because the temperature of the detecting sensor 5 does not vary or changes only insignificantly even at very low ambient temperatures; thus, the detecting sensor 5 can be operated within its specifications. By providing an incandescent lamp instead of the hitherto used light emitting diodes, the emission of light of the light source is practically not influenced by the temperature, even not by temperature fluctuations of up to 100° Kelvin; thus, the light source can be located directly in the sensor head as before. The accuracy of the measurement of the temperature is further increased by the combination thermo element/reflector, since parasitic heat flows can be substantially eliminated. Moreover, the reflector can be designed very small. By the provision of a resiliently biased element that increases the flow cross section upon decreasing barometric pressure and upon decreasing flow velocity of the air flowing through the flow channel, it can be ensured that the heat transfer between the housing of the sensor head and the ambient remains within certain limits, even if the barometric pressure varies to a substantial degree.

It is understood that instead of an incandescent lamp located in the sensor head and thus being exposed to the full range of temperatures, a light source could be provided that is located in the temperature stabilized region of the apparatus. However, this would result in the necessity to provide a second light wave conductor, with the disadvantage of a further loss in light.

With an apparatus according to the present invention, not only the requirement of an increased measuring accuracy is fulfilled, but also other requirements that are important for using such an apparatus in radio sondes, i.e. low manufacturing costs, low weight, and a low energy consumption.

As far as the embodiment of the apparatus described herein before is concerned, it is understood that this embodiment is only one possibility of realizing the invention, and that many other different embodiments of an apparatus for determining the dew-point and/or the vapor content of the air are possible within the scope of the appended claims.

What is claimed is:

1. An apparatus for determining the dew-point and/or the content of vapor in the air, for the use in a radio sondes, comprising:

a dew-point mirror assembly, including a source of light, a reflector means, a cooling element means thermally coupled to said reflector means, a temperature sensor means adapted to measure the temperature of said reflector means, and a detecting sensor means adapted to receive the light emitted by said light source and reflected by said reflector means;

a space means adapted to receive temperature sensitive components of said dew-point mirror assembly;

means for stabilizing the temperature in said space means;

said detecting sensor means being located in said space means;

said dew point mirror assembly further comprising a light wave conductor means, whereby said detecting sensor means is optically coupled to said reflector means by means of said light wave conductor means; and said temperature sensor means is constituted by a thermo element means, said thermo element means comprises two sheet metal members that are soldered to each other face to face, one of said two sheet metal members having a free surface adapted to reflect light to thereby constitute said reflector means.

2. The apparatus according to claim 1 wherein said light source is an incandescent lamp.

3. The apparatus according to claim 1 wherein said dew-point mirror assembly further comprises a sensor head means having opening means through which ambient air can flow, said reflector means being located in the interior of said sensor head means.

4. The apparatus according to claim 3 wherein said dew-point mirror assembly further comprises an active heating means adapted to heat said sensor head means.

5. The apparatus according to claim 4, further comprising a heating control means adapted to activate said active heating means in dependence of the cooling power of said cooling element means.

6. The apparatus according to claim 3 wherein said dew-point mirror assembly further comprises an active heating means adapted to heat said ambient air flowing through said sensor head means.

7. The apparatus according to claim 3, further comprising a valve means for varying the flow cross section for the ambient air flowing through said sensor head means, said valve means being adapted to operate in dependence of the barometric pressure and the flow velocity of the ambient air flowing through said sensor head means.

8. The apparatus according to claim 7 wherein said valve means comprises a resiliently biased metal plate means adapted to increase said flow cross section whenever the barometric pressure decreases and the velocity of the ambient air flowing through said sensor head means decreases.

9. The apparatus according to claim 8 wherein said infrared radiator means comprises an upper surface that is painted and a lower surface that is reflective.

10. The apparatus according to claim 9 wherein said upper surface of said infrared radiator means is blackened and said lower surface of said infrared radiator means is polished.

11. The apparatus according to claim 9 wherein said upper surface and said lower surface of said infrared radiator means are provided with an infrared permeable thermal insulation layer.

12. The apparatus according to claim 1 wherein said two sheet metal members have an overlapping portion and a free portion, said overlapping portions being soldered to each other, the free portion of one of said two sheet metal members comprising a connecting wire means welded thereon and consisting of the same material as said one of said two sheet metal members, and the free portion of the other one of said two sheet metal members comprising a connecting wire means welded thereon and consisting of the same material as said other one of said two sheet metal members.

13. The apparatus according to claim 1 wherein said thermo element means is glued to said cooling element means.

14. The apparatus according to claim 1, wherein said cooling element means is constituted by a Peltier element.

15. The apparatus according to claim 1 wherein said dew-point mirror assembly further comprises an infrared radiator means thermally coupled to the warm side of said cooling element means and located outside said space means.

16. A method for recognizing over-saturated air and/or air containing water drops or ice crystals, the method comprising the steps of:

(i) providing an apparatus for determining the dew-point and/or the content of vapor in the air, particularly for use in radio sondes, comprising:
  a dew-point mirror assembly, including an incandescent lamp, a reflector means, a cooling element means thermally coupled to said reflector means, a first temperature sensor means adapted to measure the temperature of the said reflector means, and a detecting sensor means adapted to receive the light emitted by said incandescent lamp and reflected by said reflector means;
  a space means adapted to receive temperature sensitive components of said dew-point mirror assembly;
  means for stabilizing the temperature in said space means;
  said detecting sensor means being located in said space means;
  said dew-point mirror assembly further comprising a light wave conductor means, whereby said detecting sensor means is optically coupled to said reflector means by means of said light wave conductor means; and
  said dew-point mirror assembly further comprising a sensor head means having opening means through which ambient air can flow, said reflector means being located in the interior of said sensor head means;

(ii) heating the air in the interior of said sensor head means in order to evaporate water drops or ice crystals;

(iii) determining the dew point temperature;

(iv) calculating the temperature difference between the dew point temperature and the temperature of the ambient air;

(v) recognizing the over-saturation of the air or presence of water in fluid or solid form in the air if said calculated temperature difference is positive.

17. The method according to claim 16 wherein the amount of fluid or solid water contained in a given air volume is calculated on the basis of said calculated temperature difference.

* * * * *